United States Patent [19]

Christy, Jr. et al.

[11] Patent Number: 4,948,480

[45] Date of Patent: Aug. 14, 1990

[54] KIT FOR ELECTROPHORESIS GEL MEDIUM

[75] Inventors: Kenneth G. Christy, Jr., Rochester; Hans W. Osterhoudt, Spencerport; Ignazio S. Ponticello, Pittsford, all of N.Y.

[73] Assignee: Eastman Kodak Company, Rochester, N.Y.

[21] Appl. No.: 188,821

[22] Filed: May 2, 1988

[51] Int. Cl.$^5$ .................. G01N 27/28; G01N 27/26; B01D 57/02

[52] U.S. Cl. .................. 204/182.8; 204/180.1; 204/299 R

[58] Field of Search ............. 204/182.8, 182.9, 180.1, 204/299 R

[56] References Cited

U.S. PATENT DOCUMENTS

| | | | |
|---|---|---|---|
| 4,215,195 | 7/1980 | Ponticello et al. | 430/905 X |
| 4,346,231 | 8/1982 | Ponticello et al. | 430/905 X |
| 4,582,868 | 4/1986 | Ogawa et al. | 524/211 |
| 4,704,198 | 11/1987 | Ebersole et al. | 204/182.8 |

OTHER PUBLICATIONS

U. K. Laemmli, "Cleavage of Structural Proteins During the Assembly of the Head of Bacteriophage T4," *Nature*, 1970, vol. 227, pp. 680–685.

*Primary Examiner*—John F. Niebling
*Assistant Examiner*—John S. Starsiak, Jr.
*Attorney, Agent, or Firm*—Betty J. Deaton

[57] ABSTRACT

A polyacrylamide type gel medium for electrophoresis is conveniently and safely prepared prior to use from a kit which comprises (1) a water-soluble copolymer of an acrylamide monomer and at least one comonomer copolymerizable therewith, which comonomer contains functional groups that permit crosslinking of said copolymer by a covalent but non-free radical initiated mechanism; and (2) a selected crosslinking agent in a package that separates it from the copolymer. Optionally, additional materials that may be usefully incorporated in the gel may be included in the kit, for example, a selected electrophoresis buffer and a complexing agent, such as SDS. The kit is used to prepare the gel by forming a solution of the copolymer in deionized water at the desired concentration of copolymer, adding a sufficient amount of any optional ingredients to provide the desired concentrations thereof, adding such concentration of the crosslinking agent as will provide a gelation time of between about 5 minutes and about 15 hours, and pouring the so prepared reaction mixture into a preselected mold or casting device or onto a support so as to form the resulting gel into the desired shape and size.

3 Claims, No Drawings

KIT FOR ELECTROPHORESIS GEL MEDIUM

FIELD OF THE INVENTION

This invention relates to a medium or element for electrophoresis. More particularly, it relates to a kit and method of using the kit for conveniently and safely forming a polyacrylamide type polymeric gel medium suitable for electrophoretic separation of biopolymers such as proteins or for electrophoretic separation of fragments of DNA, RNA and their derivatives.

DESCRIPTION RELATIVE TO THE PRIOR ART

U.S. Pat. No. 4,704,198, which issued on Nov. 3, 1987, contains a comprehensive description of various aspects of electrophoresis. As described therein, and in numerous other publications, electrophoresis is based on the principle that charged molecules or substances will migrate when placed in an electric field. Since proteins and other biopolymers (e.g., DNA, RNA, enzymes and some carbohydrates) are charged, they migrate at pH values different from their isoelectric points. The rate of migration depends, among other things, upon the charge density of the protein or biopolymer and the restrictive properties of the electrophoretic matrix or medium. The higher the ratio of charge to mass, the faster the ion will migrate. The more restrictive the medium, the more slowly the ion will migrate.

In theory, separation of different proteins could be achieved readily in free solution provided that the molecules differed sufficiently in their charge densities. However, in practice, separations in free solution are difficult to achieve because the heat produced during electrophoresis can cause convection disturbances which distort the protein bands. Resolution of the individual proteins is compromised because the bands are broadened. Also, band broadening continues even after the electrophoresis has been stopped because of diffusion of dissolved solute. Therefore, electrophoresis in free solution is rarely performed. In practice, various supporting media are currently used to minimize convection and diffusion, and to effect separation both on the basis of size and of molecular charge.

Many support media for electrophoresis are in current use. The most popular are sheets of paper or cellulose acetate, agarose, starch, and polyacrylamide. Paper, cellulose acetate, and similar porous materials are relatively inert and serve mainly for support and to minimize convection. Separation of proteins using these materials is based largely upon the charge density of the proteins at the pH selected.

On the other hand, starch, agarose and polyacrylamide gels not only minimize convection and diffusion but also actively participate in the separation process. These materials provide a restrictive medium in which the average size of the polymeric network opening can be controlled to achieve a molecular fractionation in a desired molecular size range. In this way, molecular sieving occurs and provides separation on the basis of both charge density and molecular size.

The extent of molecular sieving is thought to depend on how much the gel network opening size is larger than the size of the migrating particles. The network opening size of agarose gels is so large that molecular sieving of most protein molecules is minimal and separation in that medium is based mainly on charge density. In contrast, polyacrylamide gels can have openings whose sizes more closely approximate the size of protein molecules and so contribute to the molecular sieving effect. Polyacrylamide has the further advantage of being a synthetic polymer which can be prepared in highly purified form.

The ability to produce gels having a wide range of polymer concentrations, and, therefore, since the gel network opening is inversely proportional to polymer concentration, a wide range of controlled network opening sizes, as well as to form pore size gradients within the gels by virtue of polymer concentration gradients, are additional advantages of polyacrylamide as an electrophoresis gel medium. Control over opening size enables mixtures to be sieved on the basis of molecular size and enables molecular weight determinations to be performed. These determinations are especially accurate if the proteins are treated with a detergent, such as sodium dodecyl sulfate (SDS), which neutralizes the effects of molecular charge so that all SDS treated molecules, regardless of size, have approximately the same charge density values. This technique is referred to as SDS-PAGE electrophoresis.

Conventionally, polyacrylamide gel media have been prepared by free radical induced polymerization of a monomer such as acrylamide and a crosslinking agent such as N,N'-methylenebisacrylamide under oxygen-free conditions in the presence of water, a buffer, a polymerization initiator, and a polymerization catalyst. More particularly, since such polymerization can be inhibited by the presence of oxygen, polyacrylamide gel media for electrophoresis typically have been prepared by a process involving: introducing a previously deoxygenated aqueous solution containing acrylamide, a crosslinking (bis) monomer, a buffer, a free radical polymerization initiator and a polymerization catalyst into a cell formed between two glass plates with a selected clearance (e.g., 0.3-3 mm); and sealing the gel-forming solution from oxygen; whereupon the free radical polymerization proceeds so as to prepare the desired gel. Often this is done in situ by the scientist who is to conduct the electrophoresis.

The usual practice is for the manufacturer or the individual user to perform a free radical polymerization with acrylamide and a suitable bis monomer such as N,N'-methylenebisacrylamide (often simply referred to as "bis") in order to obtain a gel. Such gel formation is successfully done only as several precautions are taken, namely: (a) very high purity starting materials should be used; (b) the solution of monomers and buffer should be degassed to remove oxygen; (c) a free radical initiator and a catalyst must be quickly mixed into the degassed solution; (d) the solution should be quickly poured between two glass plates or down a glass tube, the lower end of which in either case is sealed to prevent leakage; and (e) the gelation should proceed with (i) oxygen largely excluded (i.e., to the extent feasible within the limitations of the equipment, oxygen is excluded) and (ii) adequate means for heat dissipation being present so that excess heat does not cause gel nonuniformities.

The cell employed for the preparation of the gel generally has a length of approximately 6 to 100 cm. Accordingly, the introduction of the gel-forming solution into such a long cell requires careful operation to prevent the solution from gelling before it is completely poured, thereby preventing the preparation of a uniform polyacrylamide gel medium of the desired length. Thus, the preparation of a polyacrylamide gel medium for electrophoresis having the desired length has required a great deal of skill and care, as well as keeping the solution free from oxygen.

There are several alternatives to the above-described procedure whereby the user makes electrophoresis gels by free radical polymerization and crosslinking in situ. These include (a) the use of preformed gels in cassettes and (b) the use of preformed gels on flexible supports. With either of these alternatives, however, some operating freedom or flexibility with regard to gel size, polymer content in the gel and buffer content is lost. Also—especially with precast gels in cassettes made by free radical polymerization and crosslinking—there generally remain, after completion of the gel formation reaction, some unreacted monomers. The presence of such species poses some toxicological hazards to the user and may interfere with the electrophoretic separation to be performed. Also, such precast gels have been found to have limited shelf lives.

U.S. Pat. No. 4,582,868, among others, describes the crosslinking polymerization of acrylamide-rich copolymers to form electrophoresis gel media by a non-free radical induced mechanism that does not require exclusion of oxygen. Typically, copolymers of acrylamide, optionally a difunctional monomer such as N,N′-methylenebisacrylamide that allows free radical crosslinking during polymerization, and a monomer that affords non-free radical initiated crosslinking by treatment with a crosslinking agent, for example, an acrylamide derivative such as N-[3-(2-chloroethylsulfonyl) propionamidomethyl]acrylamide,

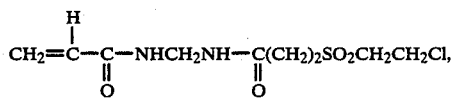

an acrylate derivative such as 2-[3-(2-chloroethylsulfonyl)propionyloxy]ethyl acrylate,

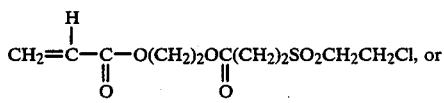

an active ester such as N-[2-(ethoxycarbonylmethoxycarbonyl)ethyl]acrylamide:

are prepared, in accordance with U.S. Pat. No. 4,582,868, by a free radical initiated polymerization in the absence of oxygen. Thereafter, the chloroethylsulfonyl group-containing polymers are crosslinked through dehydrohalogenation of the pendant chloroethylsulfonyl groups and subsequent reaction with a bis-nucleophile crosslinking agent such as a diamine. In this regard, it is noted that electrophoresis often is performed at pH values that facilitate dehydrohalogenation of the chloroethylsulfonyl groups. If the vinylsulfonyl groups so formed are not all reacted with the intended crosslinking agent, they could react with amino groups on dissolved proteins during electrophoresis. Such reaction would artifactually retard the electrophoretic migration of proteins and consequently give misleading electrophoresis results vis-a-vis the results obtained with electrophoresis gels formed by the free radical polymerization of acrylamide and bis alone.

Further, the chloroethylsulfonyl groups can dehydrohalogenate spontaneously, prior to the above crosslinking step. The dehydrohalogenated product crosslinks faster than the polymer otherwise would, giving less (i.e., inadequate) time to prepare and use the electrophoresis media.

Despite the availability of the above-described alternatives, electrophoresis media are generally prepared by the polymerization of vinyl monomers at the time of use. This necessarily involves exposure of the operator to monomers prior to use and to residual monomers during use. Such monomers are considered to be carcinogenic, and at least some are identified as neurotoxins.

The kit and method of the present invention (a) substitute a high purity, non-toxic, and moderately reactive copolymer for the neuro-toxic acrylamide and bis monomers encountered in the prior art; (b) make degassing unnecessary; (c) still require a crosslinking agent to be carefully and quickly added just before gelation and pouring; and (d) permit gelation to occur (i) in the presence of oxygen and (ii) with no necessity for heat dissipation because the crosslinking reaction generates very little heat.

SUMMARY OF THE INVENTION

The present invention provides more convenient, safer means than were heretofore available for preparing a polyacrylamide type electrophoresis gel that permits the operator to overcome several disadvantages found in the prior art. In accordance with the present invention, a kit for preparing electrophoresis gel media is provided, which kit comprises, in combination, (1) a water soluble, uncrosslinked, non-ionic copolymer of a mixture of uncharged vinyl monomers, said mixture comprising (a) at least 50%, preferably 80-98%, by weight of a monomer selected from the unsubstituted and substituted acrylamide monomers, (b) from 1 to 50%, preferably 2-20%, by weight of a monomer that contains a functional group that will enter into a crosslinking reaction by other than a free-radical initiated mechanism, and (c) from 0 to about 49% by weight of one or more monomers different from monomers (a) and (b); and (2) in a package separate from the copolymer, a crosslinking agent for reacting with the functional groups on the repeating units in the copolymer derived from monomer (b). In a preferred embodiment, the kit also includes a selected amount of electrophoresis buffer suitable for the particular electrophoresis to be conducted. Also, if the intended use is SDS-PAGE electrophoresis, the kit may further include a selected amount of SDS. However, for flexibility of use, it may be desirable for the end user to maintain separate stocks of buffer and SDS to enable him to "customize" the electrophoresis media as desired.

In the practice of the present invention, the copolymer (which may be present in the kit in dry form or in concentrated solution) is dissolved in sufficient deionized water to provide the desired concentration of polymer in the final electrophoresis gel; buffer is added to the polymer solution together with such optional ingredients as SDS (the order of addition is not critical; in fact, the buffer and other compatible optional ingredients can be admixed with the polymer in the kit, if desired); just before preparing the electrophoresis gel, there is added to the copolymer/buffer solution such concentration of the crosslinking agent as will cause gelation to occur within a time period of from about 5 minutes to about 15 hours after addition of said crosslinking agent, and then the resulting solution is formed into a gel medium of the desired dimensions by suitable electrophoresis gel shaping means, for example by pouring into a selected mold or other gel medium shaping device or coating onto a support before said gelation occurs.

The invention also provides polyacrylamide electrophoresis gel media prepared as described above. By virtue of the practice of the present invention, the exposure to neurotoxins often encountered in gelation through free radical polymerization is avoided, while the wide latitude of selection of gel dimensions, polymer concentration and buffer composition now available with conventional polyacrylamide polymerization is retained and, perhaps, enhanced.

DETAILED DESCRIPTION OF THE INVENTION

Selection and incorporation of suitable buffer is well within the knowledge of skilled workers in the electrophoresis art and depends upon the materials to be separated by the electrophoresis process in which the medium is to be employed. Such buffers and bases for selecting them are described, for example, in Andreas Chrambach, "The Practice of Quantitative Gel Electrophoresis", VCH Publishers, Deerfield Beach, Fla., U.S.A. (1985), and U. K. Laemmli, Nature, 227:680, (1970).

Also, while, as indicated, the ingredients of the kits of the present invention may be dry or in aqueous medium, to maximize shelf life and ease of handling, it is preferred that the copolymer (which must be securely separated from the crosslinking agent prior to use of the kit) be present in the kit in dry, readily dissolved, form.

Examples of suitable acrylamide monomers (a) for inclusion in the copolymers of the present invention include acrylamide, N-isopropylacrylamide, N-hydroxymethylacrylamide, N-(1,1-dimethyl-3-oxobutyl)acrylamide, N-methylmethacrylamide, 2-acrylamido-2-hydroxymethyl-1,3-propanediol, methacrylamide, N-(3-dimethylaminopropyl)acrylamide, N,N-dimethylacrylamide, N,N-diethylacrylamide, N-isopropylmethacrylamide, and 3-(2-dimethylaminoethyl)acrylamide. Particularly preferred is (unsubstituted) acrylamide.

Suitable vinyl monomers (b) having functional groups that can enter into a crosslinking reaction include:

(1) Active methyl group-containing monomers, i.e., monomers having a

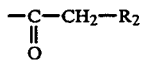

group appended thereto wherein $R_2$ is a cyano, aryl, or alkoxycarbonyl group. Suitable examples of acrylic ester monomers containing such groups, include 2-acetoacetoxyethyl acrylate, 2-acetoacetoxyethyl methacrylate, ethyl α-acetoacetoxymethylacrylate, and 2-cyanoacetoxyethyl methacrylate (described in U.S. Pat. Nos. 3,459,790 and 3,554,987). Vinyl monomers containing such groups, for example, ethyl acryloylacetate, 6-(m- and p- vinylphenyl)-2,4-hexanedione (60:40); ethyl 5-(m- and p- vinylphenyl)-3-oxopentanoate (60:40) and the corresponding methyl ester are described in U.S. Pat. Nos. 3,929,482; 3,939,130, and 3,904,418. Amide monomers containing such active methylene groups, such as N-(2-acetoacetoxyethyl)acrylamide, N-(2-acetoacetamidoethyl)methacrylamide, 4-acetoacetyl-1-methacryloylpiperazine, acetoacetamidoethyl methacrylate, and N-(3-acetoacetamidopropyl)methacrylamide are described in U.S. Pat. Nos. 4,247,673 and 4,215,195.

(2) Suitable activated halogen-containing monomers, include monomers having appended halomethylaryl, halomethylcarbonyl, halomethylsulfonyl, haloethylcarbonyl, and haloethylsulfonyl groups which will, after polymerization, also undergo crosslinking with a suitable crosslinking agent such as a diamine, dithiol, diol, etc. Monomers having such halomethylaryl groups, for example, vinylbenzyl chloride, and vinylbenzyl bromide are disclosed in U.S. Pat. No. 4,017,442. Useful monomers having appended haloethylsulfonyl groups such as m- and p-(2-chloroethylsulfonylmethyl)styrene and N-(4-chloroethylsulfonylmethyl)acrylamide are described in U.S. Pat. Nos. 4,161, 407 and 4,548,870.

Polymers having appended halomethylcarbonyl and haloethylcarbonyl groups such as chloroacetyl and chloropropionyl, are described in U.S. Pat. No. 3,625,694. Monomers which provide such crosslinkable groups include vinyl chloracetate, N-(3-chloroacetamidopropyl) methacrylamide, 2-chloroacetamidoethyl methacrylate, 4-chloracetamidostyrene, m- and p-chloracetamidomethylstyrene, N-(3-chloroacetamidocarbonyliminopropyl)methacrylamide, 2-chloroacetamidocarbonyliminoethyl methacrylate, 4-chloracetamidocarbonyliminostyrene, m- and p-chloracetamidocarbonyliminomethylstyrene, N-vinyl-N'-(3-chloropropionyl)urea, 4-(3-chloropropionamido)styrene, 4-(3-chloropropionamidocarbonylimino)styrene, 2-(3-chloropropionamido)ethyl methacrylate, and N-[2-(3-chloropropionamido)ethyl]methacrylamide.

(3) another variety of useful active halogen monomers includes those having appended triazinyl groups such as N-[3-(3,5-dichloro-1triazinylamino)propyl]methacrylamide.

(4) Active ester group-containing monomers such as disclosed in U.S. Pat. No. 4,548,870. Preferred active ester monomers are N-[2-(ethoxycarbonylmethoxycarbonyl)ethyl]acrylamide, N-(3-methacrylamidopropionyloxy)succinimide, N-(acryloyloxy)succinimide, and N-(methacryloyloxy) succinimide.

(5) Polymers having appended aldehyde groups as crosslinkable sites are also disclosed in U.S. Pat. No. 3,625,694. Monomers providing such groups are p-methacryloyloxybenzaldehyde, and vinylbenzaldehyde.

(6) Primary amino group containing monomers such as N-(3aminopropyl)methacrylamide hydrochloride, 2-aminoethyl methacrylate hydrochloride, and p-aminostyrene.

(7) Monomers having appended vinylsulfonyl and vinylcarbonyl groups such as m- & p- vinylsulfonylmethylstyrene (U.S. Pat. No. 4,161,407) and N-(3-acrylamidopropyl)methacrylamide are also useful.

(8) Monomers having appended aziridine groups such as N-acryloylaziridine, N-(N-vinylcarbamyl)aziridine, and 2-(1-aziridinyl)ethyl acrylate as described in U.S. Pat. No. 3,671,256.

(9) Monomers having appended epoxide groups such as glycidyl acrylate and glycidyl methacrylate.

A presently preferred group of monomers (b) are those of category 1 above having the structure:

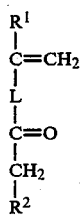

wherein R¹ is hydrogen or lower alkyl, preferably having from 1 to 8 carbon atoms, for example, methyl or propyl; R² is a cyano group or a —COR³ group wherein R³ is an alkyl, cycloalkyl, alkoxy, aryl, aryloxy, amino, alkylamino, dialkylamino, or arylamino group having from 1 to about 15 carbon atoms, for example, methyl, ethyl, phenyl, methoxy, ethoxy, diethylamino, etc.; because R² is cyano or COR³, the adjoining methylene group is an active methylene group, i.e., it has an acid hydrogen atom that is easily displaced by a nucleophile; L is a linking group selected from the group consisting of

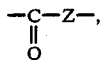

an alkylene group having 1 to 30 carbon atoms, an arylene group, or combination of two or more of said

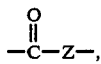

alkylene, and arylene groups, wherein Z is a divalent heterocyclic group having about 5 to 7 ring carbon and heteroatoms, for example, a 1,4-piperazinylene group.

Preferably, linking group L is a substituted or unsubstituted alkylene group have 1 to 20 carbon atoms in the backbone. This definition of alkylene is meant to include alkylene groups interrupted or terminated with heteroatom-containing radicals, for example, oxy, thio, —NR³— (wherein R³ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl, or xylyl), —Z— (as defined above), ester (—COO—), amide (—CONH—), urylene (—NHCONH—), urethane (—NHCOO—), sulfonyl (—SO₂—), carbonate, sulfonamide, azo phosphone or other similar groups. Representative alkylene groups include methylene, ethylene, isobutylene, hexamethylene, carbonyloxyethoxycarbonyl, methylenebis (iminocarbonyl), carbonyloxydodecylenecarbonyloxyethylene, carbonyliminomethyleneiminocarbonyliminoethylene, carbonyliminomethyleneiminocarbonylethylene and other groups described in U.S. Pat. No. 4,161,407 and 4,548,870.

When L is a substituted or unsubstituted arylene, it generally has 6 to 12 ring carbon atoms. Representative arylene groups include phenylene, tolylene, naphthylene, and others disclosed in U.S. Pat. Nos. 4,161,407 and 4,548,870 mentioned above. Also included in this definition of L are divalent groups which are combinations of one or more of each of the $$-\overset{O}{\underset{\|}{C}}-Z-,$$

alkylene, and arylene groups defined above (e.g., arylenealkylene, alkylenearylenealkylene, and others readily determined by one of ordinary skill in the art).

Acrylamide monomers polymerize more readily with other acrylamide monomers than do other vinyl or acrylic monomers, e.g., acrylate esters. Therefore, acrylamide monomers and monomers having amide linkages in the side chain are the preferred monomers (b) that contain the active methylene group or other group which can enter into non-free radical initiated crosslinking reactions.

Representative of the preferred active methylene group-containing monomers (b) for use in the method of the invention are:

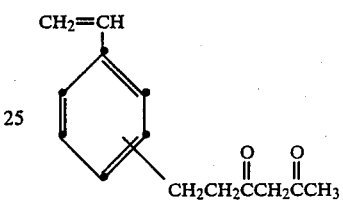

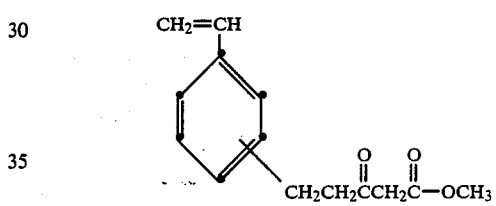

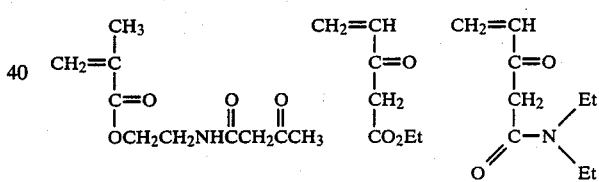

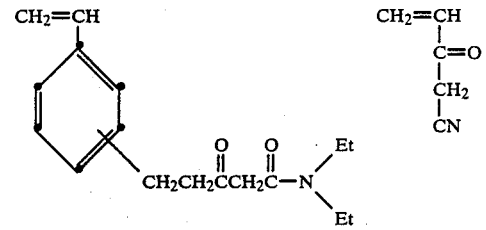

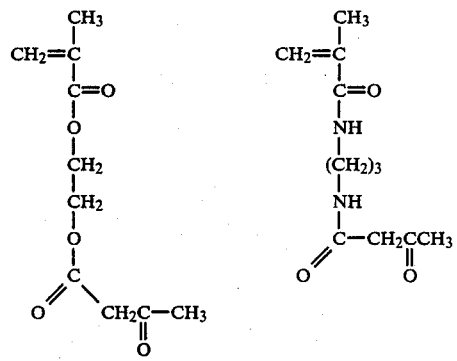

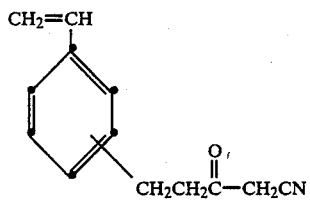
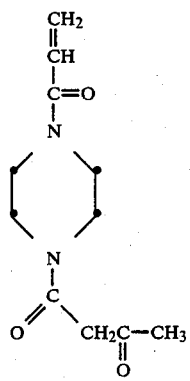
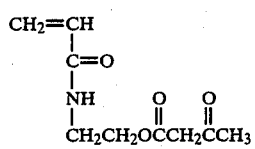

A particularly preferred polymer that contains recurring side chains having active methylene groups for use in the method of this invention is poly[acrylamide-co-N-(3-acetoacetamidopropyl)methacrylamide] wherein the weight ratio of polymerized acrylamide to N-(3-acetoacetamidopropyl) methacrylamide is 95:5.

Polymers having active methylene or primary amine groups are conveniently crosslinked with conventional gelatin hardeners such as formaldehyde, glyoxal and dialdehydes such as succinaldehyde and glutaraldehyde as described in U.S. Pat. No. 3,232,764; active esters such as described in U.S. Pat. No. 3,542,558; active halogen compounds such as described in U.S. Pat. Nos. 3,106,468, 3,305,376 and 3,957,882; s-triazines such as described in U.S. Pat. No. 3,325,287; aziridines such as described in U.S. Pat. No. 3,575,705; active olefins such as described in U.S. Pat. No. 3,490,911 and 3,640,720; vinylsulfones such as bis(vinylsulfonylmethyl)ether and bis(vinylsulfonyl)methane as described in U.S. Pat. No. 3,841,872 and U.S. Pat. No. 3,539,644; halogen-substituted aldehyde acids such as mucochloric and mucobromic acids; and polymeric hardeners such as dialdehyde starches; poly(acrolein-co-methacrylic acid); poly(acrylamide-co-2-chloroethylsulfonylmethylstyrene) and poly(acrylamide-co-vinylsulfonylmethylstryene).

Polymers having the aldehyde, activated halogen, aziridine, epoxide or active ester groups can be crosslinked with agents having two or more amino, mercapto, or hydroxy groups such as ethylenediamine, 1,3-propanediamine, 1,3-propanedithiol, dithiothreitol, dithioerythritol, and butylenediamine.

The following examples are presented to illustrate the practice of the present invention.

EXAMPLE 1 soluble polymers useful in forming electrophoresis media in accordance with the method of this invention can be prepared as described in Example 1A.

EXAMPLE 1A

Preparation of poly[acrylamide-co-N-(3acetoacetamidopropyl)methacrylamide] (Weight ratio 95/5).

To a mixture of acrylamide (electrophoresis grade) (34.2 g, 0.48 mole) and N-(3-acetoacetamidopropyl)methacrylamide (1.8 g, 0.008 moles) in Milli Q water (300 mL) and isopropanol (100 mL), maintained under a nitrogen atmosphere, was added 2,2'-azobis(2-methylpropionitrile) (2.0 g). The solution was heated at 60°–65° C. in a thermostated bath for 7 hours. The polymer was precipitated from solution by addition of the reaction mixture to acetone (3.8L), filtered, washed with methanol (4L), washed with acetone (4L), and sucked dry. The solid was redissolved in Milli Q water (275 mL), and the above procedure repeated to obtain a white solid (30.0 g, 83% yield). The polymer had an inherent viscosity of 0.32 dL/g measured at a concentration of 0.25 g/dL in a 1.0M sodium chloride solution at 25° C. Other polymers of the same family were prepared by varying the weight proportions and monomers as summarized in Table I which also lists the inherent viscosities ($\eta$) of the copolymers measured in 1.0M sodium chloride solution at a concentration of 0.25 g/dL at 25° C.

TABLE 1

| Sample | ($\eta$) |
|---|---|
| 1. Poly[acrylamide-co-N-(3-acetoacetamidopropyl)methacrylamide] (weight ratio 97.5/2.5) | 0.36 |
| 2. As 1 above except weight ratio = 90/10 | 0.30 |
| 3. As 1 above except weight ratio = 80/20 | 0.35 |
| 4. Poly[2-acrylamido-2-hydroxymethyl-1,3-propanediol-co-N-(3-acetoacetamidopropyl)methacrylamide] (weight ratio 95/5) | 0.58 |
| 5. Poly[acrylamide-co-N-(2-acetoacetoxyethyl)acrylamide] (weight ratio 90/10) | 0.97 |
| 6. As 6 above except weight ratio = 95/5 | 0.82 |
| 7. Poly[N-isopropylacrylamide-co-acrylamide-co-N-(3-acetoacetamidopropyl)methacrylamide] (weight ratio 45/45/10) | 1.16 |

EXAMPLE 1B

A 12% (w/v) electrophoresis gel was prepared from the 95:5 poly[acrylamide-co-N-(3-acetoacetamidopropyl)methacrylamide] prepared in Example 1A.

The starting copolymer solution was made by dissolving 4.84 g of the copolymer in 25.6 mL of high purity, deionized water [Milli Q]. There are (4.84) 0.05/226=1.07 ($10^{-3}$) chemical equivalents of N-(3-acetoacetamidopropyl)methacrylamide present. After dissolution of the copolymer in the water, the pH is adjusted to ca 8.8 by the addition of 10.1 mL of 1.5M "Tris" [tris(hydroxymethyl)aminomethane] buffer whose pH had previously been adjusted to 8.8 by the addition of concentrated HCl. (This buffer is designated as 1.5M Tris.HCl, and here contains 0.1 weight percent sodium dodecysulfate.) After mixing the buffer solution thoroughly into the copolymer solution and setting up the slab get casting stand, the crosslinker solution can be added.

Since, the Tris.HCl buffer (pH 8.8) competes with the active methylene site for the glyoxal crosslinker, three times the chemical equivalents of glyoxal (i.e., $3.21 \times 10^{-3}$ eq) are added. Preferably, this is added as a solution of $7(10)^{-3}$ eqcm$^{-3}$ of glyoxal in water and, in the present example, 0.46 mL of such a solution are added while the receiving buffered, copolymer solution is well stirred. Then within 1.5 minutes after the last of the crosslinker solution is added, the well mixed solution of water, copolymer, buffer, and crosslinker is poured down the 0.15 cm slot between the glass plates. This pouring typically takes up to about four minutes and should not take longer than five minutes, because the reaction between the copolymer and the glyoxal increases the molecular weight of the copolymer (and thereby the solution viscosity), making pouring more difficult. Some 20 to 25 minutes after crosslinker addition, gelation begins and then continues until the gel is firm.

EXAMPLE 2

The gel formed by following the outline just described was used for a poly(acrylamide) gel electrophoresis (PAGE) experiment in which sodium dodecylsulfate (SDS) was present as a denaturing agent for the proteins. Such experiments, which are known in the art as SDS-PAGE, are used to determine the molecular weights of proteins.

Briefly, the experimental details included the following: (a) The proteins used were two sets of known mixtures from Bio-Rad Laboratories (C/N 161-0304 and 161-0303 for the low and high molecular weight standards, respectively) that were dissolved in Tris.HCl buffer (pH 6.5) with both SDS and 2-mercaptoethanol present. These samples were completely denatured and converted to the dodecyl sulfate/protein complexes which all have approximately the same charge-to-mass ratio. The use of a buffer approximately 2 pH units below the pH of the electrode and the resolving gel buffers causes the negatively charged proteins to carry most of the current in the sample well and stacking gel, as discussed in further detail below, in the early part of the experiment; (b) a "stacking gel" of acrylamide/bis (ca 4% T( was made using Tris.HCl(pH 6.5), and the procedure as described, for example, by U. K. Laemmli, Nature, 227:680, 1970. This was placed on top of the glyoxal crosslinked resolving gel of Example 2. The Teflon comb that forms the lanes was inserted into the stacking gel solution just after it was poured. Gelation occurred in less than two hours, and the electrophoresis experiment was begun by removing the comb and loading the lanes with 40 to 50 µL of the protein standard solutions. (This procedure is referred to as "disc" or "multiphasic buffer" electrophoresis and is generally attributed to U.K. Laemmli [Nature, 227:680, 1970.] It is described in the instructions that accompany the Mini Protean II Dual Slab (Electrophoresis) Cell sold by Bio-Rad Laboratories, Richmond, Calif. 94804 (see Example 2 of this document); (c) the electrophoresis apparatus in this example was the Hoefer Model SE 400 (San Francisco, Calif. 94107), vertical slab get cell. The electrode buffers were the Tris glycinate buffer (pH 8.3) with SDS as shown on page 23 of the Bio-Rad instructions. The actual concentrations of Tris and glycine in the electrode buffers are 0.025M and 0.19M, respectively; (d) the electrical parameters for this experiment were a constant current of 30 mA until the applied voltage reached 180V, after which the voltage was held constant at 180V and the current slowly declined. It took a little over two hours for the applied voltage to rise to 180V from the initial value of 89V. The entire experiment took almost four hours.

After the electrophoresis was done, the gel was removed from between the glass plates and stained with Coomassie Blue R250 dye dissolved in a solution of methanol (40%), acetic acid (10%), and water (50%). The dye preferentially sorbed in protein-rich areas, giving dark protein bands, and leaving no doubt that electrophoretic migration according to molecular size had taken place with good resolution. A graph of the migration distances (corrected for 4.9% gel swelling in the staining solution) plotted as abscissae and the logarithm molecular weights plotted as ordinates was nearly linear, which is what one often observes for SDS-PAGE. Thus, the gel medium of this Example provided results very similar to those obtained in SDS-PAGE with gels made from acrylamide/bis polymerization.

The invention has been described in detail with particular reference to preferred embodiments thereof, but it will be understood that variations and modifications can be effected within the spirit and scope of the invention.

What is claimed is:

1. A method for preparing an electrophoresis gel medium while minimizing exposure to harmful chemicals which comprises forming a solution of the copolymer of a kit for preparing electrophoresis gel media which comprises, in combination, (1) a copolymer consisting of poly[acrylamide-co-N-(3-acetoacetaamidopropyl]methacrylamide having a weight ratio of acrylamide to the comonomer of 95:5 and (2) in a package separate from said copolymer, a crosslinking agent for reacting with the functional groups on the repeating units in the said copolymer derived from a monomer that contains a functional group that will enter into a crosslinking reaction by other than a free-radical initiated mechanism and an electrophoresis buffer in deionized water employing such proportions of said copolymer, buffer and water as to provide a gel of the desired said copolymer concentration and pH, providing means with which to form a shaped electrophoresis gel medium of the desired dimensions, adding the crosslinking agent from the kit to said solution of said copolymer and buffer in such concentration of crosslinking agent as to cause gelation to occur within a time period of from about 5 minutes to about 15 hours after said addition, and then promptly employing said gel shaping means to form the gel medium of desired dimensions from the gel thereby produced.

2. The method of claim 1 wherein said buffer is tris(-hydroxymethyl)aminoethane.

3. The method of claim 1 wherein said crosslinking agent is glyoxal.

* * * * *